United States Patent [19]

LeVahn et al.

[11] Patent Number: 5,400,772
[45] Date of Patent: Mar. 28, 1995

[54] SURGICAL RETRACTOR APPARATUS WITH IMPROVED CLAMPING DEVICE

[75] Inventors: Bruce A. LeVahn; Lee Bolduc, both of New Brighton, Minn.

[73] Assignee: Minnesota Scientific, Inc., St. Paul, Minn.

[21] Appl. No.: 705,115

[22] Filed: May 24, 1991

[51] Int. Cl.⁶ ............................................. A61B 17/02
[52] U.S. Cl. ..................... 128/20; 5/503.1; 5/658; 248/316.1; 403/256
[58] Field of Search ............... 128/20, 23; 248/316.1; 5/503.1, 658; 269/238; 403/256, 373; 606/54, 55

[56] References Cited

U.S. PATENT DOCUMENTS

| | | | |
|---|---|---|---|
| 2,670,732 | 3/1954 | Nelson | 128/20 |
| 3,522,799 | 8/1970 | Gauthier | 128/20 |
| 3,965,890 | 6/1976 | Gauthier | 128/20 |
| 4,042,232 | 8/1977 | Lile et al. | 5/503.1 X |
| 4,143,652 | 3/1979 | Meier et al. | 128/20 |
| 4,254,763 | 3/1981 | McCready et al. | 128/20 |
| 4,355,631 | 10/1982 | LeVahn | 128/20 |
| 4,696,544 | 9/1987 | Costella | 128/4 X |
| 4,971,038 | 11/1990 | Farley | 128/20 |
| 5,025,780 | 6/1991 | Farley | 128/20 |

OTHER PUBLICATIONS

Narco Scientific Pilling Division Specification Sheet, Catalog No. 99-3027, Entitled "Pilling Retractor Systems".

Primary Examiner—Richard J. Apley
Assistant Examiner—Donna L. Maraglio
Attorney, Agent, or Firm—Kinney & Lange

[57] ABSTRACT

A retractor apparatus having a hollow rod member and a clamping device is provided. Support members are adjustably secured to the hollow rod member. The clamping device includes a first member having a first clamping portion and a second member having a second clamping portion. The second member is pivotally attached to the first member. When the second member is pivoted into a clamping position with the first member, the first and second portions clamp a side rail of an operating table. A tightening mechanism retains the first and second clamping portions in the clamping position. The first member has a passage for receiving the hollow rod member.

8 Claims, 3 Drawing Sheets

5,400,772

SURGICAL RETRACTOR APPARATUS WITH IMPROVED CLAMPING DEVICE

BACKGROUND OF THE INVENTION

The present invention relates to a surgical retractor apparatus, and in particular, it relates to clamping devices that support the retractor apparatus over an operating table.

It is customary during major surgery, particularly on the chest or abdomen, to employ retractors. The retractors are applied to the edges of a surgical incision and pull back the incision exposing the area in which the surgeon must work. The retractor is held in place, typically, by being attached to a retractor apparatus that is positioned over the operating table. The retractor apparatus is usually attached to side rails located along the sides of the operating table by some type of clamping device.

In the past, many of the clamping devices on the side rails of the operating table had to be positioned in an exact location. The retractor apparatus was then secured to the clamping devices by various mechanisms to hold the retractor apparatus in place over the operating table. Since the side rails of the operating table are not sterile, a surgical drape was placed over the side rail by either cutting slits into the surgical drape and extending the supports of the retractor apparatus through the slits, or simply readjusting the drape around the support member and over the clamp and the side rail.

Some of the shortcomings of the abovementioned clamping devices are that they do not allow the placement of the retractor apparatus to be varied easily in the horizontal direction along the length of the bed unless slits are made in the surgical drape. Introducing slits into the surgical drape, to allow the supports of the retractor apparatus to engage the clamping device presents a possible danger of contamination from the unsterile surfaces of the clamping device and the side rail through the slit. In addition, vertical adjustment of the retractor apparatus is difficult since often times the clamping device is beneath the drape.

Simply readjusting the surgical drape around the support member also presents a contamination problem. If the surgical drape is moved or shifts during the operation, the unsterile clamping device and part of the side rail may be exposed.

The LeVahn U.S. Pat. No. 4,355,631, assigned to the same assignee as the present application, describes a clamping device which clamps the surgical drape to the side rail thereby preventing potential contamination problems exhibited in the other retractor apparatuses. The clamping device includes a first member having a first clamping portion and a second member having a second clamping portion. A tightening mechanism extending through the second member and bearing against the first member retains the first and second clamping portions in the clamping position against the side rail of the operating table.

Although overcoming many of the disadvantages of the other clamping devices, the LeVahn '631 patent has knobs for adjusting the clamping device and for adjusting the supports which are in close proximity to each other. Accidental release of the support could occur when the surgeon or assistant only intended to adjust the clamping device. Likewise, accidental release of the clamping device could occur when the surgeon or assistant only intended to adjust the support.

In addition, the knobs for adjusting the clamping device and for adjusting the supports of the LeVahn '631 patent are located at or below the level of the operating table. During an operation, the level of the operating table is generally below the waist-level of the surgeons. Therefore, to adjust the clamping device of the LeVahn '631 patent, the surgeon or assistant would be required to bend over or crouch down in order to visually assure that any adjustments of the clamping device or supports were done properly.

The McCready et al U.S. Pat. No. 4,254,763 describes a surgical retractor assembly having a support post with a C-type clamp for attaching the support post to a rail provided on an operating table. The C-type clamp includes a fixed first jaw member and an adjustable second jaw member which adjusts axially along the longitudinal axis of the support post. The adjustment of the second jaw member is controlled by a rotative screw mechanism extending through the support post.

SUMMARY OF THE INVENTION

The present invention includes a retractor apparatus having a clamping device. The clamping device includes a hollow rod member which sustains a support member over an operating table having side rails. The clamping device further includes a first member having a first clamping portion and a second member having a second clamping portion. The first member is pivotally attached to the second member. The first and second clamping portions engage the side rail when the second member is pivoted into a clamping position. The first and second clamping portions are pivoted into and held in the clamping position by a tightening mechanism. The first member also includes a passage which extends therethrough through which the hollow rod member extends.

DETAILED DESCRIPTION OF THE PREFERRED EMBODIMENTS

Figure 1:
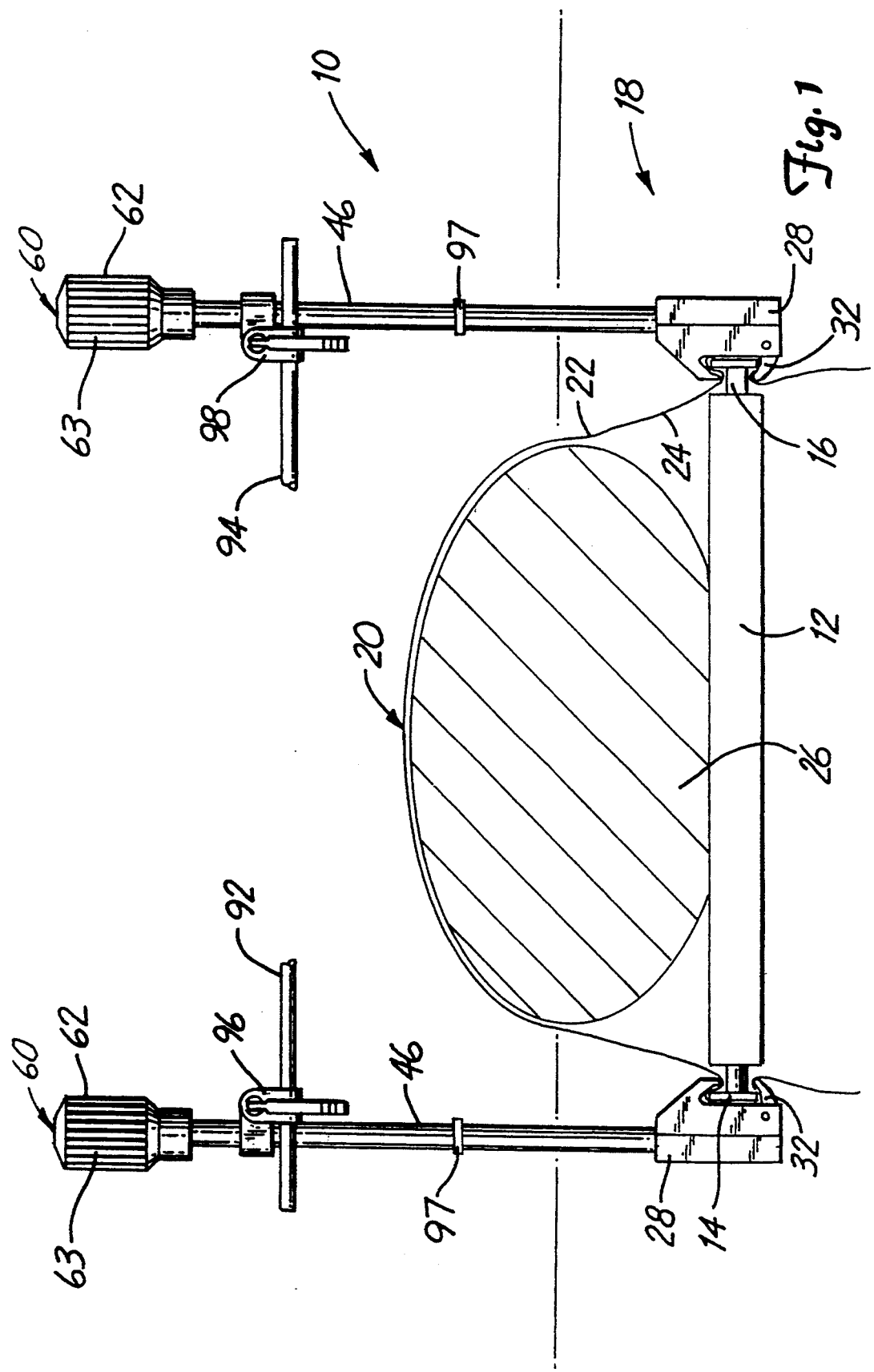
FIG. 1 is an elevational view of the retractor apparatus of the present invention in use, with an operating table and a body to be operated on upon the operating table, the body and the operating table being illustrated in cross-section.

In FIG. 1, a retractor apparatus 10, together with a clamping device 18, is illustrated in connection with an operating table 12. The operating table 12 is of conventional construction. Rigidly secured to each side of the operating table 12 is a side rail 14. The side rail 14 is spaced outwardly from the bed and is secured thereto by a plurality of posts 16.

The clamping device 18 secures the retractor apparatus 10 to the side rail 14. Preferably, the clamping device 18, in addition to securing the retractor apparatus 10, will also secure a surgical drape 20 by clamping the surgical drape 20 against the side rail 14. The surgical drape 20 is a conventional surgical drape having been sterilized and, when placed on an operating table 12, has a side which is maintained sterilized and a side which is not maintained sterilized. The side which is maintained sterilized is referred to as sterilized side 22 and the side which is not maintained sterilized is referred to as unsterilized side 24. The surgical drape 20 is placed over a body 26, the body 26 tending to be unsterilized, to prevent infection in the area of the incision.

Figure 2:
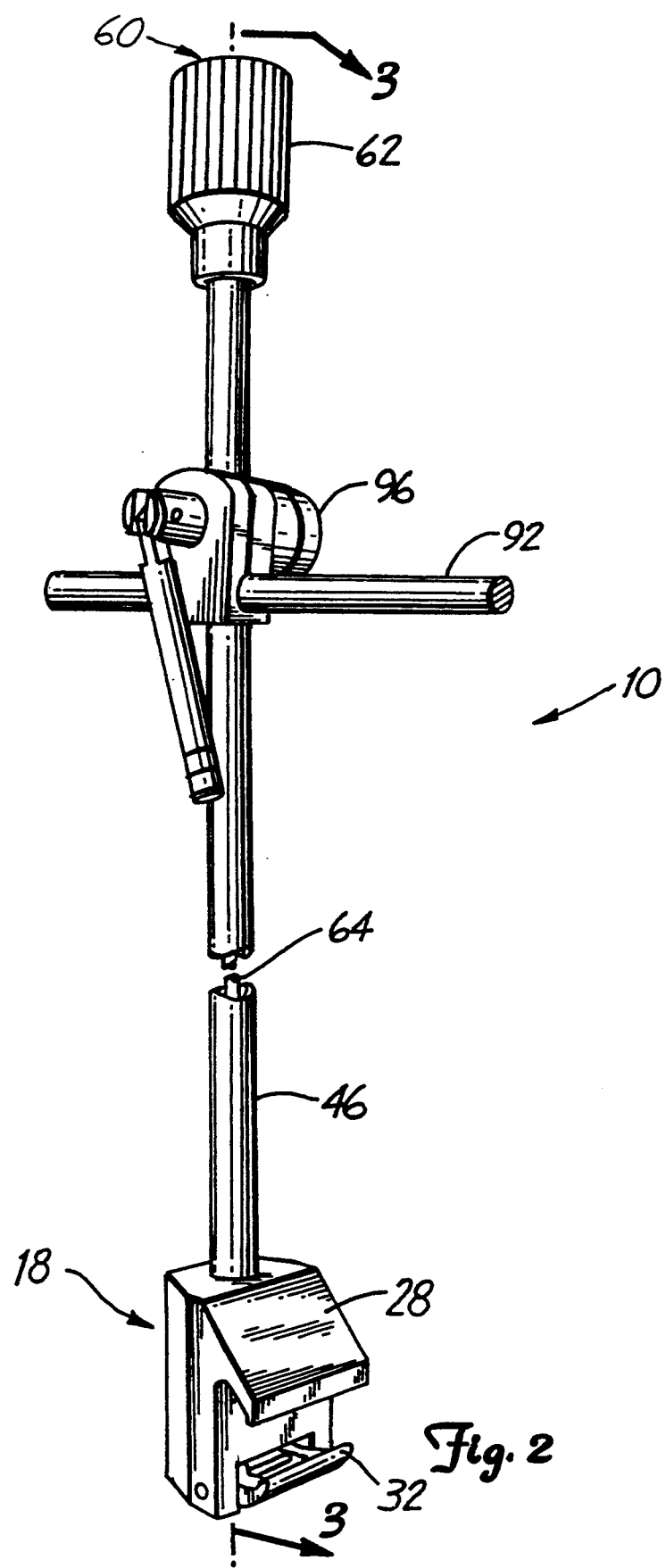
FIG. 2 is a perspective view of the retractor apparatus with the clamping device of the present invention.
Figure 3:
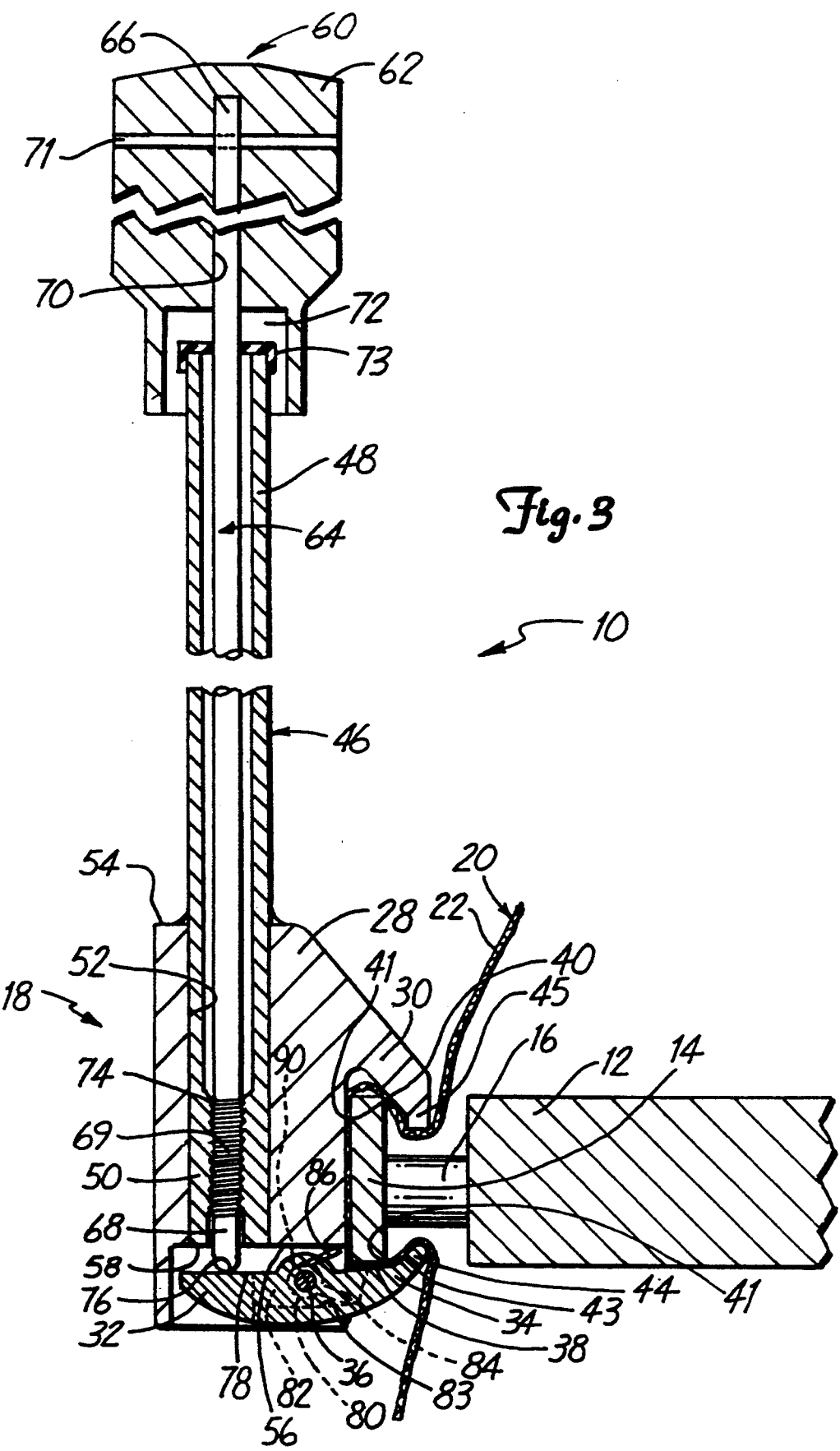
FIG. 3 is a sectional view of the clamping device taken along the line 3—3 in FIG. 2, with the spring being illustrated in phantom.

The clamping device 18 is illustrated in more detail in FIGS. 2 and 3. As illustrated in FIG. 3, the clamping device 18 includes an upper member 28 with an upper clamping portion 30 for engagement with the side rail 14 over the surgical drape 20. A lower member 32 with a lower clamping portion 34 is pivotally attached to the upper member 28, preferably by a pivot pin 36. The lower clamping portion 34 of the lower member 32, similarly, engages the side rail 14 over the surgical drape 20.

The lower clamping portion 34 preferably has a substantially planar surface 38 and a lower beveled edge 43. The upper clamping portion 30 preferably has an upper beveled edge 40. The upper and lower beveled edges 40 and 43 define a gripping edge that grips the back corners 41 of the side rail 14.

The lower member 32 pivots to a clamping position about the pivot pin 36 with the upper and lower clamping portions 30 and 34 gripping the side rail 14 and holding the surgical drape 20 in place. The upper and lower clamping portions also include an upper and a lower lip portion 45 and 44, respectively. The upper and the lower lip portions 45 and 44 serve as stops to prevent the clamping device 18 from dislodging from the side rail 14 in case the retractor apparatus 10 is accidentally jarred or impacted.

The upper and lower clamping portions 30 and 34, although illustrated gripping one surgical drape 20 having a particular thickness against a side rail 14 having a rectangular cross-section, can actually grip a plurality of surgical drapes, each having various thicknesses, against various cross-sectional configurations of side rails.

A spring 80 provides a biasing force to the upper member 28 and the lower member 32, tending to bias the upper and lower clamping portions 30 and 34 apart. The spring 80 preferably sits in a depression 82 that is machined in the lower member 32. The spring 80 has a lower spring member 84 contacting a depression surface 83 of the depression 82 and an upper spring member 86 contacting a bottom edge surface 56 of the upper member 28. A loop 90 of the spring 80 surrounds the pivot pin 36 to hold the spring 80 securely within the depression 82. It should be understood that although the present invention has been described using a particular type of spring, any type of biasing mechanism is within the scope of the present invention.

The clamping device 18 supports the retractor apparatus 10 by engaging a hollow rod member 46 having a first end portion 48 and a second end portion 50. A passage 52 preferably extends through the upper member 28 in a substantially vertical direction perpendicular to the longitudinal axis of the side rail 14. The passage 52 extends from a top edge surface 54 of the upper member 28 to the bottom edge surface 56. The passage 52 is sized and shaped to receive the hollow rod member 46.

To assemble the retractor apparatus 10 of the present invention, the second end portion 50 of the hollow rod 46 is inserted into the passage 52 through the top edge surface 54 until the hollow rod 46 passes entirely through the passage 52. The hollow rod 46 continues through the passage 52 until an end surface 58 of the second end portion 50 of the hollow rod 46 is aligned with the bottom edge surface 56. The second end portion 50 of the hollow rod 46 is fastened to the upper member 28 at the top edge surface 54 by welding or other conventional means such that the hollow rod 46 is fixedly secured within the passage 52. This type of fastening allows the clamping device 18 to retain the hollow rod member 46 in a fixed position with respect to the operating table 12 and prevents blood or other substances from entering the passage 52 between the hollow rod 46 and the upper member 28.

The clamping device 18 is held in the clamping position around the side rail 14 by a tightening mechanism 60. The tightening mechanism 60 includes a clamping knob 62 and a cylindrical threaded shaft 64. The clamping knob 62 is preferably sized such that a hand can comfortably grasp and easily rotate the clamping knob 62. In addition, as illustrated in FIG. 1, the clamping knob 62 includes a fluted surface 63 to allow the surgeon or assistant to grasp and easily manipulate the clamping knob 62. Although a fluted surface 63 is illustrated, any type of gripping surface may be used on the clamping knob 62 such as surfaces including knurls, raised bumps or the like.

As illustrated in FIG. 3, the cylindrical shaft 64 includes an upper end portion 66, a lower end portion 68 and a threaded portion 69. The clamping knob 62 further includes a bore 70 sized and shaped to receive the upper end portion 66 of the cylindrical shaft 64. The upper end portion 66 of the cylindrical shaft 64 is fixedly held within the bore 70 by a fastening stake 71 or by other conventional means.

The cylindrical shaft 64 is enclosed within the hollow rod 46. A cap member 73 having an aperture 75 therethrough is attached to the first end portion 48 with the cylindrical shaft 64 being snugly received within the aperture 75. The cap member 73 caps the hollow rod 46 to assist in preventing blood or other substances from entering the hollow rod 46 and to assist in maintaining the cylindrical shaft 64 in the substantial center of the hollow rod 46.

The clamping knob 62 is situated about the cap member 73 and the first end portion 48 of the hollow rod 46 opposite the clamping device 18. The clamping knob 62 additionally includes a recessed portion 72 which receives the cap member 73 and the first end portion 48 of the hollow rod 46. The recessed portion 72 is sized and shaped such that the clamping knob 62 is allowed to freely rotate circumferentially about the cap member 73 and the first end portion 48.

As illustrated in FIG. 3, the threaded portion 69 of the cylindrical shaft 64 threadably engages a threaded passage 74 within the hollow rod 46. The clamping device 18 is placed in the clamping position by turning the clamping knob 62 thereby threading threaded portion 69 of the cylindrical shaft 64 through the threaded passage 74. The threaded portion 69 of the cylindrical shaft 64, when threaded into the threaded passage 74, forces a lower end surface 76 of the cylindrical shaft 64 into contact with an upper surface 78 of the lower member 32. This action causes the lower member 32 to pivot about the pivot pin 36 with the lower clamping portion 34 moving toward the upper clamping portion 30. The clamping device 18 is in the clamping position when the tightening mechanism 60 cannot be turned further by using reasonable force.

To disengage the upper and lower clamping portions 30 and 34 from the clamping position, the clamping knob 62 is turned in an opposite direction 10 withdrawing the lower end surface 76 from the upper surface 78 of the lower member 32. Therefore, when the tightening mechanism 60 is turned to release the clamping device 18 from the clamping position, the spring 80 cooperates with the tightening mechanism 60 in moving the clamping portions 30 and 34 away from the side rail 14 and surgical drape 20.

In use, the surgical drape 20 is placed over the patient with the lower end of the surgical drape 20 lying on the operating table 12. The surgical drape 20, being sterilized, provides a sterile environment for the forthcoming operation on the patient. The clamping device 18, also being sterile, is clamped at the appropriate position over the lower end of the surgical drape 20 onto the side rail 14. The clamping device 18 is clamped onto the side rail 14 by turning the clamping knob 62 and forcing the lower end surface 76 of the cylindrical shaft 64 against the upper surface 78 of the lower member 32. The lower member 32 will pivot to the clamping position in cooperation with the upper member 28 thereby securing the retractor apparatus 10 to the side rail 14 of the operating table 12.

As illustrated in FIG. 1, adjustably secured to the hollow rod 46 are retractor clamps 96 and 98 such as the clamping device or retractor clamps described in copending application Ser. No. 07/394,578, assigned to the same assignee as the present application. In addition, a ring 97 is securely fastened around the hollow rod 46 to tend to prevent the retractor clamps 96 and 98 from contacting the upper member 28. The retractor clamps 96 and 98 are movable along the length of the hollow rod 46 between the clamping knob 62 and the ring 97.

Longitudinal support members 92 and 94, which are preferably of circular cross-section, extend through apertures in the retractor clamps 96 and 98, respectively. Various surgical retractor implements can be adjustably secured to the support members 92 and 94. The surgical retractor implements are designed to hold the portions of the body 26 along the edges of a surgical incision in a manner as to expose the area on which the surgeon must work.

The entire retractor apparatus 10 is easily adjusted along the horizontal length of the operating table 20 by simply turning clamping knob 62 to unclamp the clamping device 18 and moving the clamping device 18 along the side rail 14. To adjust the retractor apparatus 10 in the vertical direction, the retractor clamps 96 and 98 are released. The retractor clamps 96 and 98 are then adjusted and the retractor clamps 96 and 98 are secured to retain the support members 92 and 98 in a fixed position.

Since the clamping device 18 is on the sterile side 22 of the surgical drape 20, both vertical and horizontal adjustments are easily made without endangerment to the sterile environment from contamination underneath the surgical drape 20. In addition, the clamping device 18 of the present invention holds the surgical drape 20 in place over the operating table 12.

Furthermore, both the clamping knob 62 for adjusting the horizontal movement of the retractor apparatus 10 and the retractor clamps 96 and 98 for adjusting the vertical movement of the surgical retractor implements are generally situated above the waist-level of the surgeon or assistant. This allows adjustment of the retractor apparatus 10 in both the horizontal and vertical directions by either the surgeon or the assistant while they are in the standing position without having to bend over or crouch down in order to visually assure that adjustments of the clamping device or supports was done properly.

Although the present invention has been described with reference to preferred embodiments, workers skilled in the art will recognize that changes may be made in form and detail without departing from the spirit and scope of the invention.

What is claimed is:

1. A clamping device for supporting a retractor apparatus over an operating table, the clamping device comprising:
   a hollow rod member;
   a first member having a passage therethrough and a first clamping portion to clamp the clamping device to a side rail of the operating table, the first member being attached to the hollow rod member;
   a second member pivotally attached to the first member, the second member having a second clamping portion to clamp the retractor apparatus to the side rail, the second member pivoting to a clamping position with the first clamping member; and
   means for tightening the first and second clamping portions into the clamping position, the means for tightening extending through the hollow rod member and the passage of the first member and cooperating with the second member to pivot the second member into the clamping position.

2. The device of claim 1 wherein the hollow rod member is welded to the first member.

3. The device of claim 1 wherein the hollow rod member is received within the passage of the first member.

4. The device of claim 1 wherein the operating table is covered by a surgical drape having a sterile and an unsterile side and the clamping devices support the retractor apparatus on the sterile side of the surgical drape covering the operating table.

5. The device of claim 4 wherein the first clamping portion of the first member and the second clamping portion of the second member engage the sterile side of the surgical drape to clamp the unsterile side of the surgical drape against the side rail.

6. The device of claim 1 wherein the means for tightening the first and second clamping portions comprises a tightening mechanism engaging the second member such that the second clamping portion is pivoted toward the first clamping portion.

7. The device of claim 6 wherein the tightening mechanism includes a clamping knob from which a threaded shaft extends, the shaft threadably engaging and extending through the hollow rod member which has a threaded portion therein, and the shaft engaging the second member such that the second clamping portion is pivoted toward the first clamping portion as the clamping knob is tightened.

8. The device of claim 1 and further including a spring bias means for biasing the second clamping portion away from the first clamping portion.

* * * * *